United States Patent [19]

Vora

[11] 4,324,937
[45] Apr. 13, 1982

[54] CONVERSION OF PROPANE AND BUTANE INTO GASOLINE

[75] Inventor: Bipin V. Vora, Elk Grove Village, Ill.

[73] Assignee: UOP Inc., Des Plaines, Ill.

[21] Appl. No.: 220,546

[22] Filed: Dec. 29, 1980

Related U.S. Application Data

[63] Continuation-in-part of Ser. No. 112,484, Jan. 16, 1980, Pat. No. 4,275,255.

[51] Int. Cl.³ .................................................. C07C 2/58
[52] U.S. Cl. .................................. 585/315; 585/314; 585/331; 585/332; 585/654; 585/723; 585/734
[58] Field of Search .................... 585/315, 331, 332

[56] References Cited

U.S. PATENT DOCUMENTS

| | | | |
|---|---|---|---|
| 2,314,435 | 3/1943 | Allender | 585/332 |
| 2,389,984 | 11/1945 | Jones | 585/332 |
| 2,999,074 | 9/1961 | Bloch et al. | 252/442 |
| 3,073,878 | 1/1963 | Johnson | 585/712 |
| 3,080,438 | 3/1963 | Sailors | 585/701 |
| 3,112,351 | 11/1963 | Hoekstra | 585/748 |
| 3,128,319 | 4/1964 | Meisinger et al. | 585/734 |
| 3,391,218 | 7/1968 | Bloch | 585/660 |
| 3,409,540 | 11/1968 | Gould et al. | 208/79 |
| 3,448,165 | 6/1969 | Bloch | 585/660 |
| 3,527,715 | 9/1970 | Giannetti et al. | 252/415 |
| 3,647,719 | 3/1972 | Hayes | 252/466 PT |
| 3,647,911 | 3/1972 | Vesely et al. | 585/660 |
| 3,649,704 | 3/1972 | Hayes | 585/482 |
| 3,652,697 | 3/1972 | Hayes | 585/482 |
| 3,686,354 | 8/1972 | Hervert | 585/331 |
| 3,714,281 | 1/1973 | Hayes et al. | 585/433 |
| 3,742,078 | 6/1973 | Hayes | 585/434 |
| 3,745,112 | 7/1973 | Rausch | 208/139 |
| 3,755,481 | 8/1973 | Hayes | 585/434 |
| 3,789,082 | 1/1974 | Cook et al. | 585/748 |
| 3,867,473 | 2/1975 | Anderson | 585/716 |
| 3,904,384 | 9/1975 | Kemp et al. | 44/56 |
| 3,925,502 | 12/1975 | Boney et al. | 585/720 |
| 3,931,352 | 1/1976 | Mikulicz | 585/332 |
| 4,139,573 | 2/1979 | Carson | 585/701 |
| 4,161,497 | 7/1979 | Makovec et al. | 585/714 |

OTHER PUBLICATIONS

The Oil and Gas Journal, R. F. Anderson, "Changes Keep HF Alkylation Up-to-Date", Feb. 11, 1974, pp. 78–82.

Primary Examiner—Curtis R. Davis
Attorney, Agent, or Firm—James R. Hoatson, Jr.; John F. Spears, Jr.; William H. Page, II

[57] ABSTRACT

A hydrocarbon conversion process for the production of motor fuel blending stocks from propane and butane is disclosed. Preferably a charge stream comprising a mixture of $C_3$-$C_4$ saturated hydrocarbons is split into a $C_3$ stream passed into a dehydrogenation zone and a $C_4$ stream passed into an isostripper column. Normal butanes are removed from the isostripper and passed into an isomerization zone, with product isobutane being concentrated by fractionation in the isostripper. Isobutane and propylene from the dehydrogenation zone are then reacted in an alkylation zone which produces $C_5$-plus product hydrocarbons. The effluent of the alkylation zone enters the isostripper. The product stream and a propane-containing stream are withdrawn from the isostripper, with the propane-containing stream being passed into a second separation zone. Alternative butane fractionation systems are disclosed.

15 Claims, 1 Drawing Figure

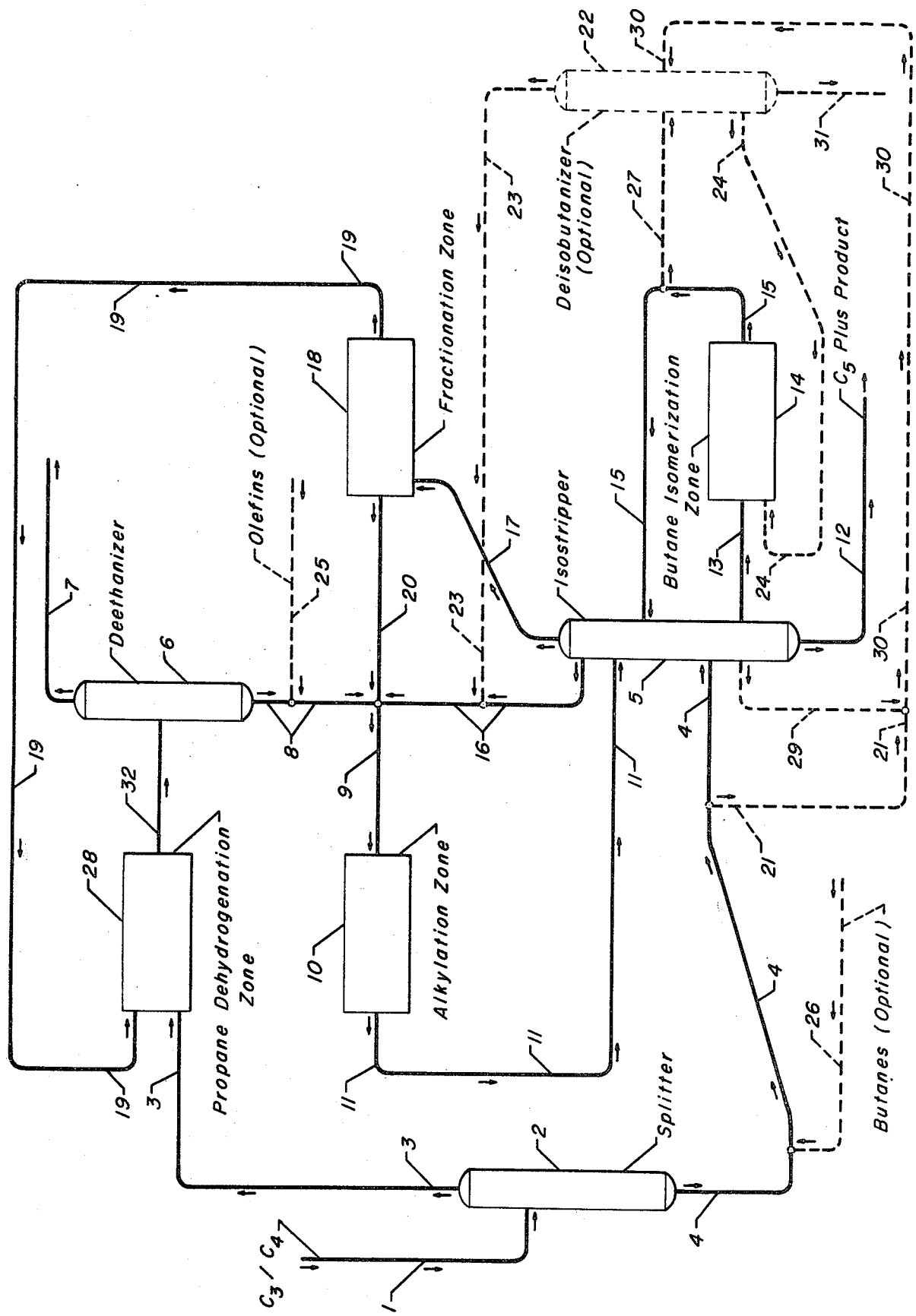

CONVERSION OF PROPANE AND BUTANE INTO GASOLINE

CROSS-REFERENCE TO RELATED APPLICATION

This application is a continuation-in-part of my prior copending application Ser. No. 112,484 filed Jan. 16, 1980, and now U.S. Pat. No. 4,275,255. The teaching of my prior application is incorporated herein by reference.

FIELD OF THE INVENTION

The invention is a multi-step hydrocarbon conversion process for the production of motor fuel blending components from saturate $C_3$ and $C_4$ hydrocarbons. The process comprises the individual steps of fractionation, isomerization of normal butane, dehydrogenation of propane, and alkylation of isobutane with propylene. Processes of this nature are described in U.S. Patents classified in Classes 585 and 208.

PRIOR ART

The production of motor fuel by the alkylation of light paraffins with $C_3$ and/or $C_4$ olefins is a widely practiced commercial process. Liquid phase hydrofluoric acid (HF) is often employed as the catalyst. This process is described in U.S. Pat. Nos. 3,073,878; 3,080,438; 3,686,354; 3,867,473 (Cl. 260-683.49); 3,925,502 (Cl. 260-683.48); 4,139,573 (Cl. 260-683.49); and 4,161,497 (Cl. 585-714). The process is also described in the article starting at page 78 of the Feb. 11, 1974 issue of *The Oil and Gas Journal.* These references describe process conditions, process equipment, regeneration of the HF, and fractionation and treating procedures required in the process.

The isomerization of normal paraffins is described in U.S. Pat. Nos. 2,999,074; 3,112,351; 3,128,319; 3,527,715 (Cl. 252-415); 3,649,704 (Cl. 260-668A); 3,652,697 (Cl. 260-668A); and 3,789,0812 (Cl. 260-683.68).

Processes for the dehydrogenation of paraffins are described in U.S. Pat. Nos. 3,391,218 (Cl. 260-683.3); 3,448,165 (Cl. 260-683.3); 3,647,719 (Cl. 252-466PT); 3,647,911 (Cl. 260-683.3); 3,714,281 (Cl. 260-668D); 3,742,078 (Cl. 260-668D); and 3,755,481 (Cl. 260-668D). These references describe the catalyst and process conditions which may be employed in the dehydrogenation of butanes. The preferred dehydrogenation catalyst is described in U.S. Pat. No. 3,745,112 (Cl. 208-139).

A multi-step process in which normal butanes are isomerized and the resultant isobutane is consumed in an alkylation zone by reaction with olefinic hydrocarbons is described in U.S. Pat. No. 3,931,352 (Cl. 260-683.49). U.S. Pat. No. 3,409,540 also illustrates the sequential steps of butane isomerization and alkylation.

U.S. Pat. No. 3,904,384 (Cl. 44-56) describes a multi-step process in which gasoline blending components are produced from normal butane and isobutane. The process includes the steps of fractionation, normal butane isomerization, thermal dehydrogenation of the isobutane and etheration of the isobutylene with isopropanol which is also produced in the process.

A multi-step process in which gasoline blending components are produced is described in U.S. Pat. No. 2,314,435. This process includes the steps of fractionation, normal butane isomerization, butane dehydrogenation and alkylation, but has a different overall flow and does not address the consumption of propane.

BRIEF SUMMARY OF THE INVENTION

The invention provides a process for the conversion of saturate butanes and propane into gasoline. The preferred embodiment of the invention may be broadly characterized as a hydrocarbon conversion process which comprises fractionating a charge stream which comprises propane and butane into a first feed stream which is rich in propane and a second feed stream which is rich in butane; passing the first feed stream and a propane-rich recycle stream into a dehydrogenation zone and producing a dehydrogenation zone effluent stream comprising propane and propylene; passing the second feed stream into a first fractionation zone; withdrawing a normal butane-rich first process stream from the first fractionation zone and passing the first process stream into a butane isomerization zone to produce an isomerization zone effluent stream which comprises isobutane and normal butane; passing the isomerization zone effluent stream into the first fractionation zone; transferring a net overhead stream from the first fractionation zone into a second fractionation zone wherein the net overhead stream is separated to produce the previously referred to propane recycle stream and an isobutane-rich second process stream; passing the dehydrogenation zone effluent stream, the second process stream and an isobutane-rich third process stream withdrawn from the first fractionation zone into an alkylation zone and thereby producing an alkylation zone effluent stream comprising propane, butane and $C_7$–$C_8$ aliphatic hydrocarbons; passing the alkylation zone effluent stream into the first fractionation zone; and withdrawing a product stream comprising $C_5$-plus aliphatic hydrocarbons from the first fractionation zone.

In a second embodiment of the invention a deisobutanizer column is employed. This column is fed the second feed stream, the butane isomerization zone effluent stream and a process stream comprising normal butanes removed from the first fractionation zone and produces an isobutane-rich overhead stream passed into the alkylation zone and a normal butane-rich sidecut stream which is passed into the butane isomerization zone.

DETAILED DESCRIPTION

There has been a constantly increasing demand for high octane gasoline blending stocks. This is in part the result of the gradual phase down in the use of lead anti-knock compounds in gasoline. It also results from the steadily increasing number of motor vehicles which must be fueled with lead-free gasoline to prevent damage to the catalytic converters used in pollution reduction systems. For these and other reasons, it has become increasingly important to maximize both the quantity and the octane number of gasoline which is produced from available hydrocarbon feedstocks.

New facilities for the recovery of light hydrocarbons, such as propane and butane, which were previously wasted by flaring close to the site of their production are now coming on-stream in several Mideastern countries. There is presently no shortage of propane or butane on a worldwide basis, and the added production of propane and butane may result in there being an actual surplus of these light hydrocarbons. It is an objective of the subject invention to provide a hydrocarbon conversion process for producing high octane motor fuel blending stocks. It is also an objective of the subject invention to provide an improved process for converting a mixture of propane and butane into gasoline.

It is preferred that a single charge stream containing propane, isobutane and normal butane is fed to the subject process. However, it is also possible for the process to receive separate propane and butane feed streams. A single charge stream would be divided into propane-rich and butane-rich feed streams as the initial step in the process, and most of the description herein will therefore be based on the premise that such a single stream is fed into an initial propane-butane splitter column. It is preferred that this charge stream contains over 95 mol.% $C_3$ and $C_4$ saturate hydrocarbons and that the stream contains as little ethane and unsaturated hydrocarbons as is practical. The presence of pentane in amounts up to several mol.% is acceptable.

The overall flow of two basic embodiments of the inventive concept are presented in the Drawing. A charge stream comprising a mixture of propane and butane enters the process through line 1 and is passed into a splitter column 2. This fractionation column is designed and operated to separate the entering hydrocarbons into a net overhead stream carried by line 3 which is substantially free of butane and a butane-rich bottoms stream carried by line 4. The net overhead stream of the feed splitter column is referred to herein as the first feed stream. This stream and a propane recycle stream carried by line 19 are passed into a propane dehydrogenation reaction zone 28 wherein these streams are contacted with a dehydrogenation catalyst at dehydrogenation conditions effective to produce an effluent stream which comprises propane, propylene and light ends including hydrogen, methane and ethane. This effluent stream is passed into a deethanizer column 6 which is normally considered to be part of the overall propane dehydrogenation zone. The deethanizer functions to concentrate the great majority of the light ends into a net overhead stream removed from the process through line 7 and a net bottoms stream carried by line 8 which is referred to herein as the propane dehydrogenation zone effluent stream.

Substantially all of the butane present in the charge stream carried by line 1 is concentrated into a feed splitter bottoms stream carried by line 4 and passed into an isostripper column 5. This bottoms stream is also referred to as the second feed stream, and the isostripper is also referred to as the first fractionation zone. Depending on the butane concentration in the charge stream carried by line 1, an optional stream of butane carried by line 26 may be admixed into the hydrocarbons carried by line 4 to increase the total amount of butane charged to the process. The great majority of the normal butanes which enter the isostripper 5 are concentrated into a lower sidecut stream removed from the isostripper in line 13 and passed into a butane isomerization zone 14. In this zone the entering butanes are contacted with a butane isomerization catalyst at isomerization conditions chosen to effect the formation of a butane isomerization zone effluent stream which comprises isobutane and normal butane. The isomerization zone effluent stream is passed into the isostripper at an upper intermediate point through line 15.

The isostripper column 5 produces a net overhead stream carried by line 17 which comprises HF, isobutane and propane. This overhead stream is passed into a fractionation zone 18 (the second fractionation zone) and separated into a recycle stream, which is rich in propane, carried by line 19 and a second stream carried by line 20 comprising the heavier hydrocarbons such as isobutane which enter the fractionation zone. This second process stream is combined with an upper sidecut stream comprising isobutane which is removed from the isostripper through line 16 and with the dehydrogenation zone effluent stream carried by line 8 and passed into line 9 as the feed hydrocarbons for the alkylation zone 10. These feed hydrocarbons are intimately contacted with an alkylation catalyst, preferably liquid phase HF, under alkylation-promoting conditions to produce a hydrocarbon phase effluent stream carried by line 11 which comprises the product $C_7$ and $C_8$ alkylate, unreacted normal butane and a small amount of propane. The alkylation zone effluent stream is passed into the isostripper at an upper intermediate point, with the alkylate being recovered as part of the $C_5$-plus net bottoms stream of the isostripper removed from the process in line 12.

Alternative embodiments of the invention are also shown in the Drawing. One of these variations is the passage of an additional feed stream comprising $C_3$, $C_4$, or $C_3$ and $C_4$ olefins into the process through line 25. This supplementary olefinic feed stream could be admixed with any of the hydrocarbon streams being passed into the alkylation zone 10 or if desired, could be passed into the deethanizer 6 to utilize this column as either a deethanizer or a drying column.

In a major variation of the flow of the subject process, a portion or all of the butane stream flowing through line 4 is passed into an optional deisobutanizer column 22 through lines 21 and 30 instead of into the isostripper. Also charged to the deisobutanizer column is the effluent stream of the butane isomerization zone 14 through lines 15 and 27. A portionn or all of the normal butane-rich sidecut stream of the isostripper may be removed in line 29 instead of line 13 and passed into the deisobutanizer via line 30. The deisobutanizer column is designed and operated to separate the entering hydrocarbons into a net overhead stream carried by line 23 which is rich in isobutane and a net bottoms stream removed from the column in line 31 which contains substantially all of the $C_5$-plus hydrocarbons which enter the deisobutanizer. The deisobutanizer overhead stream is admixed with the isostripper upper sidecut stream carried by line 16 and is eventually passed into the alkylation zone. The deisobutanizer bottoms stream is removed from the process separately or in admixture with the isostripper bottoms stream. Also withdrawn from the deisobutanizer column is a normal butane-rich sidecut stream carried by line 24. This stream is passed into the butane isomerization zone to recycle normal butane for conversion to isobutane. Not shown in this Drawing are the alumina treaters or other means which would be employed in conjunction with the use of HF as the alkylation catalyst to prevent the passage of fluorine-containing compounds into the dehydrogenation and isomerization zones.

The subject process utilizes two fractionation zones and may include an optional deisobutanizer column. It is preferred that both the first and the second fractionation zones comprise a single trayed column. If correctly designed and operated a column having 70 trays is suitable as the first fractionation zone (isostripper) and a column having 35 trays is suitable for use as the second fractionation zone.

The dehydrogenation zone will contain a reaction zone comprising one or more reactors and such auxiliary process equipment as is required for the operation of the reaction zone. The auxiliary equipment will include the customary heat exchangers, separators, heaters, coolers, etc., found on many dehydrogenation process units. The effluent of the reaction zone is normally cooled, compressed and then recooled to condense most of its $C_3$ hydrocarbons to thereby form a hydrogen-rich gas which is recirculated within the dehydrogenation zone to supply the desired hydrogen to hydrocarbon ratio withinn the reaction zone. It is preferred that the resulting liquid phase is then passed into a fractionation column operated as a deethanizer to produce a $C_3$-plus dehydrogenation zone effluent stream and a light gas stream which is withdrawn from the process. This light gas stream will contain hydrogen and dehydrogenation by-products such as $C_1$ and $C_2$ hydrocarbons. The reaction zone of the dehydrogenation zone preferably comprises at least one radial flow reactor in which the catalyst gradually moves downward by gravity flow to allow the continuous replacement of used catalyst with catalyst having a higher activity. It is preferred that a multi-stage zone in which the reactants make at least two passes through a catalyst bed is employed. A detailed description of moving bed reactors of this type may be obtained by reference to U.S. Pat. Nos. 3,647,680; 3,652,231; 3,706,536; 3,785,963; 3,825,116; 3,839,196; 3,839,197; 3,854,887; and 3,856,662.

The particular dehydrogenation conditions employed within the reaction zone will vary depending on such factors as the catalyst activity, and the desired conversion. The conditions which may be employed for propane dehydrogenation include a temperature of from about 550° C. to 800° C., a pressure of from about 0.5 to about 20 atmospheres and a liquid hourly space velocity of about 0.5 to 20 hr.$^{-1}$. The preferred propane dehydrogenation conditions are a temperature of from about 600° C. to 700° C., a pressure of 1.0 to 3.0 atmospheres, a liquid hourly space velocity of about 1 to 8 hr.$^{-1}$ and a hydrogen to total hydrocarbon ratio between 1.0:1.0 and 5.0:1.0.

The preferred propane dehydrogenation catalyst is comprised of a platinum group component, a tin component and an alkali metal component with porous inorganic carrier material. Other catalytic compositions may be used within this zone if desired.

It is preferred that the porous carrier material of the dehydrogenation catalyst is an absorptive high surface area support having a surface area of about 25 to about 500 m$^2$/g. The porous carrier material should be relatively refractory to the conditions utilized in the reaction zone and may be chosen from those carrier materials which have traditionally been utilized in dual-function hydrocarbon conversion catalysts. A porous carrier material may therefore be chosen from an activated carbon, coke or charcoal, silica or silica gel, clays and silicates including those synthetically prepared and naturally occurring, which may or may not be acid-treated, as for example attapulgus clay, diatomaceous earth, kieselguhr, bauxite; refractory inorganic oxides such as alumina, titanium dioxide, zirconium dioxides, magnesia, silica-alumina, alumina-boria, etc.; crystalline aluminosilicates such as naturally occurring or synthetically prepared mordenite or a combination of one or more of these materials. The preferred porous carrier material is a refractory inorganic oxide, with the best results being obtained with an alumina carrier material. The crystalline aluminas, such as gamma-alumina, give the best results. In general the preferred catalysts will have a gamma-alumina carrier which is in the form of spherical particles having a relatively small diameter on the order of about 1/16-inch.

The preferred alumina carrier material may be prepared in any suitable manner. For example, the alumina carrier may be prepared by adding a suitable alkaline reagent, such as ammonium hydroxide, to a salt of aluminum such as aluminum chloride in an amount to form an aluminum hydroxide gel which upon drying and calcining is converted to alumina. It is particularly preferred that alumina spheres are manufactured by the well-known oil drop method which comprises forming an alumina hydrosol by the techniques taught in the art, and preferably by reacting aluminum metal with hydrochloric acid, and combining the hydrosol with a suitable gelling agent. The resultant mixture is dropped into an oil bath maintained at elevated temperatures. The droplets remain in the oil bath until they set and form hydrogel spheres. The spheres are then continuously withdrawn from the oil bath and are normally subjected to specific aging treatments in oil and an ammoniacal solution to further improve their physical characteristics. The resulting pellets are then washed and dried at relatively low temperatures of about 150° C. to about 200° C. and calcined at a temperature of about 450° C. to about 700° C. for a period of about 1 to about 20 hours. See the teachings of U.S. Pat. No. 2,620,314 for additional details on the preparation of the base material by the oil drop method.

The preferred dehydrogenation catalyst also contains a platinum group component. Of the platinum group metals, which include palladium, rhodium, ruthenium, osmium and iridium, the use of platinum is preferred. The platinum group component may exist within the final catalyst composite as a compound such as an oxide, sulfide, halide, oxysulfide, etc., or as an elemental metal or in combination with one or more other ingredients of the catalyst. It is believed that best results are obtained when substantially all the platinum group component exists in the elemental state. The platinum group component generally comprises from about 0.01 to about 2 wt.% of the final catalytic composite, calculated on an elemental basis. It is preferred that the platinum content of the catalyst is between about 0.1 and 1.0 wt.%. The preferred platinum group component is platinum, with palladium being the next preferred metal. The platinum group component may be incorporated into the catalyst composite in any suitable manner such as by coprecipitation or cogelation with the preferred carrier material, or by ion-exchange or impregnation of the carrier material. The preferred method of preparing the catalyst normally involves the utilization of a water-soluble, decomposable compound of a platinum group metal to impregnate the calcined carrier material. For example, the platinum group component may be added to the support by commingling the support with an aqueous solution of chloroplatinic or chloropalladic acid. An acid such as hydrogen chloride is generally added to the impregnation solution to aid in the distribution of the platinum group component throughout the carrier material.

The tin component of the preferred catalyst should constitute about 0.01 to about 5 wt.% of the final composite, calculated on an elemental basis, although substantially higher amounts of tin may be utilized in some cases. Best results are often obtained with about 0.1 to about 1 wt.% tin. It is preferred that the atomic ratio of tin to platinum is between 1:1 and about 6:1. The tin component may be incorporated into the catalytic composite in any suitable manner known to effectively disperse this component in a very uniform manner throughout the carrier material. Thus, the component may be added to the carrier by coprecipitation. A preferred method of incorporating the tin component involves coprecipitation during the preparation of the preferred carrier material. This method typically involves the addition of a suitable soluble tin compound, such as stannous or stannic chloride to an alumina hydrosol, mixing these ingredients to obtain a uniform distribution throughout the sol and then combining the hydrosol with a suitable gelling agent and dropping the resultant admixture into the oil bath as previously described. The tin component may also be added through the utilization of a soluble, decomposable compound of tin to impregnate the calcined porous carrier material. A more detailed description of the preparation of the carrier material and the addition of the platinum component and the tin component to the carrier material may be obtained by reference to U.S. Pat. No. 3,745,112.

The preferred propane dehydrogenation catalyst contains less than 0.5 wt.% halogen and preferably less than 0.1 wt.% halogen. Residual amounts of any halogen, such as chlorine, at or below this concentration may be tolerated. The preferred catalyst does however contain an alkali metal component chosen from cesium, rubidium, potassium, sodium, and lithium. The preferred alkali metal is lithium. The concentration of the alkali metal may range from between 0.1 and 3.5 wt.% but is preferably between 0.2 and about 1.5 wt.% calculated on an elemental basis.

The normal butane-rich stream removed from the isostripper or from the deisobutanizer is passed into a butane isomerization zone. This zone comprises a reactor and auxiliary process equipment such as heaters, condensers, separatory vessels, etc. The isomerization zone also contains a stripping column which eliminates hydrogen and light ends (methane and ethane) from the net effluent of the isomerization zone. With the preferred catalyst, this stripping column will also remove volatile chloride compounds from the isomerization zone effluent. The core of the operation of this zone is passage of the sidecut stream through a reactor maintained at butane isomerization-promoting conditions including the presence of an acidic isomerization catalyst. This is normally a relatively low pressure operation performed at a pressure of from about 50 to 600 psig. and at an elevated temperature as required by the activity of the catalyst. The average reactant temperature may be as high as 500° C., but is preferably between 100° C. and 320° C. It is normal practice to pass the butane through the reactor in admixture with between 1 and 10 moles of hydrogen per mole of butanes to ensure vapor phase conditions and to suppress coke deposition on the catalyst. It is preferred that the butane is passed vertically through one or more fixed beds of catalyst located within the reactor at a liquid hourly space velocity between 1.0 and 6.0, but space velocities in the broad range of 0.5 to 12.0 can be employed if desired. The effluent of the isomerization reactor is normally separated into a hydrogen-rich recycle gas which is returned to the reactor and an isomerate-containing liquid stream. It is within the scope of the inventive concept that this liquid stream may be fractionated to allow the recycling of normal butanes and the achievement of higher conversionn rates, but this is not preferred. Further details on the butane isomerization step of the subject process may be obtained by referring to the previously cited references.

The preferred isomerization-promoting catalyst for use in the isomerization zone comprises a platinum group component and a halogen component supported by an inorganic oxide carrier. In general, the carrier material is a porous, high surface area material which is relatively refractory to the conditions utilized in the isomerization process. The carrier material may be selected from silica, alumina, titanium dioxide, chromium, or mixtures of these oxides; various naturally occurring refractory oxides in different degrees of purity, such as bauxite and bentonite clay; or a diatomaceous earth such as kieselguhr. Of the above-mentioned oxides, alumina is preferred and particularly preferred is a synthetically prepared substantially anhydrous gamma-alumina with a high degree of purity.

The preferred platinum group component is platinum, palladium or a mixture of platinum and palladium. This however is not intended to exclude the other platinum group metals such as rhodium, ruthenium, osmium and iridium. A platinum group component may exist within the final catalytic composite as an oxide, a sulfide or a halide, etc., or as an elemental metal. On a weight basis, the platinum group component will comprise only a minor fraction of the total catalytic material. The preferred catalyst will therefore contain less than about 2.0 wt.% of the platinum group component, with the preferred concentration being from about 0.05 to about 1.0 wt.%. The method by which the platinum group component is made part of the catalytic composite is not controlling. It may therefore be added by coprecipitation or cogelation with the preferred carrier material or by ion-exchange or impregnation on the pre-existing carrier material. The preferred method of preparing the catalyst impregnates the carrier material by contacting it with an aqueous solution of a water-soluble, decomposable compound of a platinum group metal. This may be performed by dipping the carrier material in a solution of chloroplatinic acid, ammonium chloroplatinate, bromoplatinic acid, or platinum dichloride. The utilization of a platinum chloride compound is preferred since it facilitates the incorporation of both the platinum component and at least a minor quantity of the halogen component in a single step.

There are also numerous ways in which to add the halogen component to the isomerization catalyst. The halogen component may be composited with the carrier material during the impregnation of the carrier material with the platinum group component by the utilization of a mixture of chloroplatinic acid and hydrogen chloride. Alternatively, the alumina hydrosol which is typically utilized to form the preferred alumina carrier material may contain at least a portion of the halogen. The halogen may also be added by contacting a calcined carrier material with an aqueous solution of an acid such as hydrogen chloride, hydrogen fluoride, or hydrogen bromide, etc. The halogen component may be selected from chlorine, fluorine, iodine, bromine or mixtures thereof with chlorine and fluorine being particularly preferred. The halogen component is normally referred to as a combined halogen and is typically present in an amount of from 0.01 to about 5.0 wt.% based on the dried support material.

A particularly preferred method for the production of an isomerization catalyst is presented in U.S. Pat. No. 2,999,074. The carrier material and the platinum group component are composited and the resulting material is mildly calcined. This calcination is normally carried out under carefully controlled conditions to remove physically adsorbed solvents such as water but to retain some chemically combined hydroxyl groups on the surface of the catalyst. Temperatures ranging from 350° C. to about 700° C. are usually satisfactory. The calcined composite is then reacted with a metal halide of the Friedel-Crafts type. Suitable metal halides include aluminum chloride, aluminum bromide, ferric chloride and zinc chloride, etc. Of these, aluminum chloride is particularly preferred.

Recently developed isomerization catalysts are of a bimetallic or trimetallic nature. An example of this is the catalytic composite comprising a platinum group component, a germanium component, and a Friedel-Crafts metal halide component shown in U.S. Pat. No. 3,649,704. In U.S. Pat. No. 3,652,697, there is disclosed a trimetallic catalyst comprising a platinum group component, a germanium component, a rhenium component and a Friedel-Crafts metal halide component.

The net hydrocarbon effluent of the isomerization zone is a mixture of isobutane and normal butane. This stream is passed into the isostripper or into the deisobutanizer if it is present. Substantially all of the isobutane which enters the isostripper or the deisobutanizer is concentrated into a net overhead stream and eventually passed into the alkylation zone.

Also, the net $C_3$-plus effluent of the dehydrogenation zone and the isobutane-rich stream produced in the process are passed into an alkylation zone. These different streams may be admixed prior to their passage into the alkylation zone. The dehydrogenation zone effluent stream may contain some butylene formed by the dehydrogenation of butane present in the feed stream to the dehydrogenation zone. This butylene is consumed in the alkylation zone in the same manner as propylene by reaction with isobutane.

The term "alkylation zone" is intended to indicate a sequence of processing equipment in which the entering reactants are contacted with an alkylation catalyst maintained at alkylation-promoting conditions including one or more reaction zones and the required equipment for the separation and recovery of the resultant alkylate from process streams circulating within the alkylation zone. It is preferred that the alkylation zone contains no fractionation columns other than that used for catalyst regeneration.

The alkylation reaction is promoted by the presence of a mineral acid catalyst such as hydrofluoric acid, sulfuric acid or phosphoric acid. These acids are maintained in a liquid phase containing a minimum of water to reduce corrosion problems. The maximum amount of water normally allowed in the acid is less than 5 wt.%. When fresh acid is charged to a plant, it is normally very dry and contains about 0.5 wt.% water or less. The catalyst may also comprise a mixture of a mineral acid and a Friedel-Crafts metal halide promoter such as aluminum chloride, aluminum bromide, boron trifluoride and other proton donors.

Alkylation conditions in general include a pressure sufficient to maintain the hydrocarbons and acid in a liquid phase, with a general range being from about 20 psig. to about 500 psig., and a more preferred range being from 100 psig. to about 250 psig. It is preferred that the pressure within the reactant-catalyst contacting vessel is approximately 150 psig. and essentially "floats" on the pressure maintained in the downstream fractionation zone. Although the alkylation reaction may be performed at temperatures from below −18° C. to about 90° C., it is preferred to operate the commercially prevalent isoparaffinolefin alkylation process in the range of from about 10° C. to about 60° C., with 32° C. being a representative and particularly preferred operating temperature.

Typical operating conditions in the alkylation zone include a high ratio of the concentration of the paraffinic or other alkylatable material to the concentration of the olefinic material in order to produce a high quality alkylate by encouraging monoalkylation instead of polymerization. A broad range of this ratio is from about 6 to about 20 with a preferred operating range being from 8 to 12. A second ratio which varies in competing alkylation processes is the ratio of the acid to the hydrocarbons in the total emulsion formed, that is, the ratio in the material charged to the mixing zone or reaction point. This ratio may vary widely from a high of about 10:1 to a low of about 0.5:1, but it is preferred that the subject process is operated at an acid to hydrocarbon ratio of about 2:1.

There are a great number of olefin-isoparaffin alkylation processes known to those skilled in the art. The great majority of these processes will operate within the range of alkylation conditions set out above. They would however have substantial differences in equipment and flow paths used in performing the alkylation. These variations are attempts to obtain optimum quality alkylate by varying the method of contacting the monoolefin with the isoparaffin. Since this reaction occurs very rapidly, and also because hydrofluoric acid will catalyze the polymerization of the mono-olefin, the standard alkylation methods consist of either first admixing acid-free streams of olefin and isoparaffin to form a reactant mixture which is then admixed with the hydrofluoric acid, or an acid-free olefin stream is mixed with an acid-containing isoparaffin stream. In either case, a large number of ventures or mixing nozzles are normally utilized to widely disperse the olefin-containing stream into the acid-containing stream.

The resulting alkylation reaction is very exothermic and it is therefore necessary to provide means to remove the heat of reaction. This is normally done either by providing indirect heat-exchange means within the reacting mixture or by cooling one of the reactant streams, normally the acid stream, prior to passing it to the reaction zone. Mixing the acid and hydrocarbon feed stream results in the formation of an emulsion, and it is preferred that this emulsion be maintained by the continued agitation of the emulsion since this results in the removal of fluorides from the alkylate and the improvement of the octane number of the resulting alkylate. The maintenance of the emulsion is normally effected by its passage through a mixer or soak zone comprising a vessel having a number of internal obstructions which produce substantial turbulence as the emulsion passes through them. The emulsion is then typically fed into some type of settling vessel wherein a gravity separation of the emulsion is performed. The acid phase is removed for recirculation, and the recirculated acid may be cooled to remove the heat of reaction. The hydrocarbon phase removed from the settling vessel is passed into the isostripper as the alkylation zone effluent stream. This hydrocarbon phase will comprise mainly alkylate and the excess isoparaffin which was fed to the alkylation zone. Some processes do not utilize a soak zone at all and still others contact the separated hydrocarbon phase with a regenerated high strength acid stream to aid in defluorination. Further details on the design and operation of reaction vessels, the overall operation of the alkylation step, the regeneration of the preferred HF catalyst, etc., may be obtained by reference to the previously cited references.

The net hydrocarbonaceous effluent stream of the alkylation zone is passed into the isostripper or first fractionation zone. This isostripper is similar to that normally associated with HF catalyst motor fuel alkylation units. The isostripper recovers the alkylate which consists of $C_7$ and $C_8$ aliphatic hydrocarbons and other $C_5$-plus hydrocarbons as a net bottoms stream removed as the product of the process. When HF is used as the alkylation catalyst, the bottoms stream contains a small amount of isopentane produced in the alkylation zone. The sidecut stream rich in isobutane and the sidecut stream rich in normal butane are removed from the isostripper for recycling through the process. If HF is utilized as the catalyst in the alkylation zone, fluoride compounds will normally be present in these recycle streams. These process streams should then be passed through a fluoride removal zone comprising an alumina treater and a caustic contacting zone when the fluoride compounds will be detrimental to any catalyst which they may subsequently contact. This is often the case which chloride-promoted isomerization catalysts. Such treatment is required with the preferred isomerization and dehydrogenation catalyst. Therefore, any portion of a fluoride-containing recycle stream which is passed into either the dehydrogenation or isomerization zones should be treated for the removal of fluorides. This includes the propane recycled from the second fractionation zone to the dehydrogenation zone.

The embodiment of the invention which includes the use of the optional deisobutanizer column may be characterized as a hydrocarbon conversion process which comprises the steps of passing a first feed stream, which is rich in propane, and a recycle stream which is also rich in propane into a dehydrogenation zone operated at dehydrogenation conditions and producing a dehydrogenation zone effluent stream which comprises propane and propylene; passing a second feed stream, which is rich in butanes, and a first process stream comprising normal butane and which is withdrawn from a first fractionation zone into a deisobutanizer column, and withdrawing from the deisobutanizer column a first deisobutanizer stream which is rich in isobutane and a second deisobutanizer stream which is rich in normal butane; passing the second deisobutanizer stream into a butane isomerization zone operated at isomerization conditions and producing an isomerization zone effluent stream which comprises isobutane and normal butane; passing the isomerization zone effluent stream into the deisobutanizer column; transferring a net overhead stream which comprises propane and isobutane from the first fractionation zone to a second fractionation zone wherein the net overhead stream is separated into the previously referred to propane-rich recycle stream and a second process stream which is rich in isobutane; passing the dehydrogenation zone effluent stream, the second process stream, a third process stream which is rich in isobutane and is withdrawn from the first fractionation zone and the first deisobutanizer stream into an alkylation zone operated at alkylation conditions and thereby producing an alkylation zone effluent stream which comprises normal butane, propane and $C_7$ aliphatic hydrocarbons; passing the alkylation zone effluent stream into the first fractionation zone; and, withdrawing a product stream comprising $C_7$ aliphatic hydrocarbons from the first fractionation zone.

Any reference herein to a stream as being "rich" in any particular chemical compound or class of compounds is intended to indicate that the stream contains at least 50 mol.%. of the specified compound or compounds. Any usage herein of the term "substantially" and similar terms is intended to designate a quantitative value of at least 90 mol.%. For instance, a statement that substantially all of a compound is removed from a stream is to be construed as the removal of over 90 mol.% of the compound.

I claim as my invention:

1. A hydrocarbon conversion process which comprises the steps of:
   (a) passing a first feed stream which is rich in propane and a recycle stream which also is rich in propane into a dehydrogenation zone operated at dehydrogenation conditions and producing a dehydrogenation zone effluent stream which comprises propane and propylene;
   (b) passing a second feed stream, which is rich in butanes into a first fractionation zone;
   (c) withdrawing a first process stream, which is rich in normal butane, from the first fractionation zone and passing said first process stream into a butane isomerization zone operated at isomerization conditions and producing an isomerization zone effluent stream which comprises isobutane and normal butane;
   (d) passing the isomerization zone effluent stream into the first fractionation zone;
   (e) transferring a net overhead stream which comprises propane and isobutane from the first fractionation zone to a second fractionation zone wherein the net overhead stream is separated into the previously referred to propane-rich recycle stream and a second process stream, which is rich in isobutane;
   (f) passing the dehydrogenation zone effluent stream, the second process stream and a third process stream, which is rich in isobutane and is withdrawn from the first fractionation zone, into an alkylation zone operated at alkylation conditions and thereby producing an alkylation zone effluent stream which comprises normal butane, propane and $C_7$–$C_8$ aliphatic hydrocarbons;
   (g) passing the alkylation zone effluent stream into the first fractionation zone; and,
   (h) withdrawing a product stream comprising $C_5$-plus aliphatic hydrocarbons from the first fractionation zone.

2. The process of claim 1 further characterized in that a third feed stream comprising propylene is passed into the alkylation zone.

3. The process of claim 1 further characterized in that a third feed stream comprising a butylene is passed into the alkylation zone.

4. The process of claim 1 further characterized in that the first and the second feed streams are produced by fractionating a charge stream comprising propane, isobutane and normal butane.

5. The process of claim 4 further characterized in that the first fractionation zone comprises a single fractionation column.

6. The process of claim 5 further characterized in that liquid phase HF is utilized as a catalyst in the alkylation zone.

7. The process of claim 4 further characterized in that a third feed stream comprising a butane is passed into the first fractionation column.

8. A hydrocarbon conversion process which comprises the steps of:
(a) passing a first feed stream, which is rich in propane, and a recycle stream which is also rich in propane into a dehydrogenation zone operated at dehydrogenation conditions and producing a dehydrogenation zone effluent stream which comprises propane and propylene;
(b) passing a second feed stream, which is rich in butanes, and a first process stream comprising normal butane and which is withdrawn from a first fractionation zone into a deisobutanizer column, and withdrawing from the deisobutanizer column a first deisobutanizer stream which is rich in isobutane and a second deisobutanizer stream which is rich in normal butane;
(c) passing the second deisobutanizer stream into a butane isomerization zone operated at isomerization conditions and producing an isomerization zone effluent stream which comprises isobutane and normal butane;
(d) passing the isomerization zone effluent stream into the deisobutanizer column;
(e) transferring a net overhead stream which comprises propane and isobutane from the first fractionation zone to a second fractionation zone wherein the net overhead stream is separated into the previously referred to propane-rich recycle stream and a second process stream which is rich in isobutane;
(f) passing the dehydrogenation zone effluent stream, the second process stream, a third process stream which is rich in isobutane and is withdrawn from the first fractionation zone and the first deisobutanizer stream into an alkylation zone operated at alkylation conditions and thereby producing an alkylation zone effluent stream which comprises normal butane, propane and $C_7$ aliphatic hydrocarbons;
(g) passing the alkylation zone effluent stream into the first fractionation zone; and,
(h) withdrawing a product stream comprising $C_7$ aliphatic hydrocarbons from the first fractionation zone.

9. The process of claim 8 further characterized in that a third feed stream comprising isobutane and normal butane is passed into the deisobutanizer column.

10. The process of claim 9 further characterized in that the first fractionation zone comprises a single fractionation column.

11. The process of claim 10 further characterized in that liquid phase HF is utilized as a catalyst in the alkylation zone.

12. The process of claim 8 further characterized in that the first and the second feed streams are produced by fractionating a charge stream comprising propane, insobutane and normal butane.

13. The process of claim 8 further characterized in that a third feed stream comprising propylene is passed into the alkylation zone.

14. The process of claim 8 further characterized in that a third feed stream comprising a butylene is passed into the alkylation zone.

15. The process of claim 8 further characterized in that the first process stream also comprises $C_7$ aliphatic hydrocarbons and in that a third deisobutanizer stream which is rich in $C_7$-plus hydrocarbons is removed from the deisobutanizer column as a bottoms stream.

* * * * *